United States Patent [19]

Wallquist et al.

[11] Patent Number: 5,476,949
[45] Date of Patent: Dec. 19, 1995

[54] FINELY DIVIDED HIGHLY TRANSPARENT DIKETOPYRROLOPYRROLE PIGMENTS

[75] Inventors: Olof Wallquist, Marly; Gary Wooden, Oberschrot; Thomas Eichenberger, Basel; Ingo Schlöder, Matran, all of Switzerland

[73] Assignee: Ciba-Geigy Corporation, Tarrytown, N.Y.

[21] Appl. No.: 278,594

[22] Filed: Jul. 21, 1994

[30] Foreign Application Priority Data

Jul. 29, 1993 [CH] Switzerland .............................. 2297/93

[51] Int. Cl.$^6$ .............................. C07D 487/04; C08K 5/34
[52] U.S. Cl. .............................. 548/453; 524/92; 524/597; 524/720
[58] Field of Search .............................. 548/453

[56] References Cited

U.S. PATENT DOCUMENTS

| | | | |
|---|---|---|---|
| 4,415,685 | 11/1983 | Iqbal et al. | 524/92 |
| 4,579,949 | 4/1986 | Rochat et al. | 546/167 |
| 4,659,775 | 4/1987 | Pfenninger et al. | 524/92 |
| 4,720,305 | 1/1988 | Iqbal et al. | 106/288 |
| 4,931,566 | 6/1990 | Surber et al. | 548/453 |
| 5,342,955 | 8/1994 | Wooden et al. | 548/255 |

FOREIGN PATENT DOCUMENTS

| | | |
|---|---|---|
| 0061426 | 9/1982 | European Pat. Off. . |
| 0094911 | 9/1982 | European Pat. Off. . |
| 0181290 | 5/1986 | European Pat. Off. . |
| 0302018 | 2/1989 | European Pat. Off. . |
| 0511165 | 1/1993 | European Pat. Off. . |

*Primary Examiner*—David B. Springer
*Attorney, Agent, or Firm*—Michele A. Kovaleski

[57] ABSTRACT

Finely divided 1,4-diketopyrrolo[3,4-c]pyrroles of the formula

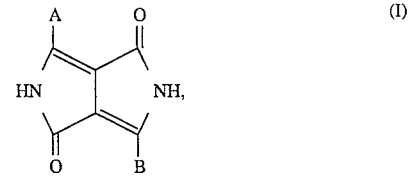

where A and B are each independently of the other a radical of the formula

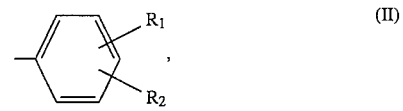

wherein at least 84% by weight of the particles have a Stokes equivalent diameter of $\leq 0.25$ μm, and mixtures thereof.

The substituents $R_1$ and $R_2$ are defined in claim 1.

These pigments are notable for a very pure hue and outstanding transparency.

22 Claims, No Drawings

FINELY DIVIDED HIGHLY TRANSPARENT DIKETOPYRROLOPYRROLE PIGMENTS

The present invention relates to novel finely divided diketopyrrolopyrrole pigments of high purity and transparency which have a certain particle size distribution, and to the production thereof.

1,4-Diketopyrrolo[3,4-c]pyrrole pigments have been known for some years and are described for example in U.S. Pat. Nos. 4,415,685 and 4,579,949. Some have proved useful in demanding applications. Recently the demand for high transparency pigmentary forms, especially for the production of metallic effect coatings, has risen appreciably. The problem is therefore to prepare such highly praised pigments in a pure high transparency form.

U.S. Pat. No. 4,579,949 describes the preparation of 1,4-diketopyrrolo[3,4-c]pyrroles by reacting a dialkyl succinate with nitriles in the presence of a strong base and subsequent hydrolysis of the resulting salt. It is stated that the hydrolysis should be carried out in water, in an alcohol having 1 to 4 carbon atoms or preferably in an acid and that more transparent pigmentary forms are produced when the hydrolysis is carried out at below 80° C. (by hydrolysis is meant here the conversion of the pigment alkali metal salts into the corresponding pigment, i.e. the protonation of the pigment alkali metal salts).

U.S. Pat. No. 4,659,775 discloses processes for preparing specific alkyl diketopyrrolopyrroles and asymmetrical diketopyrrolopyrroles starting from enamine diesters and pyrrolinones, respectively. It is apparent from this later application that the hydrolysis is preferably to be carried out in water. As regards transparent forms, it is also proposed that the hydrolysis be carried out at below 80° C. The message is similar from the likewise subsequently published U.S. Pat. No. 4,720,305, which concerns the preparation of diketopyrrolopyrrole pigment mixtures from succinic diesters and two different nitriles. This publication too gives preference to carrying out the hydrolysis in water. For the preparation of transparent forms, however, a subsequent comminution, for example by aqueous wet grinding, is recommended.

U.S. Pat. No. 4,931,566 describes a process for preparing particularly pure pyrrolo[3,4-c]pyrroles which is characterized in that the hydrolysis is carried out sequentially in at least two steps, with an inorganic and/or organic acid, with water and alcohol or with an inorganic or organic acid, water or/and alcohol, preferably at between 50° and 100° C. Nothing is said about transparency. The products which are mentioned specifically are without exception all opacifying pigments.

It has now been found that the specific combination of three measures in the preparation, namely discharging the pigment salt suspension onto water and/or alcohol, temperatures between −20° and 50° C., presence of an acid yields certain finely divided diketopyrrolopyrrole pigments wherein at least 84% by weight of the particles have a Stokes equivalent diameter (D 84) of <0.25 μm and which exhibit surprisingly, previously unattainably, high purity and transparency. The particle size distribution (D 84) is determined by methods known per se, following dilution of a varnish mill base, by photosedimentometry (see Example 10).

The present invention accordingly provides 1,4-diketopyrrolo[3,4-c]pyrroles of the formula

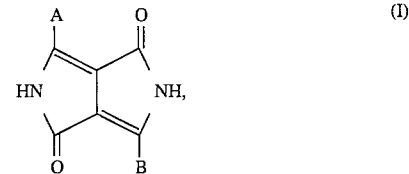

where A and B are each independently of the other a radical of the formula

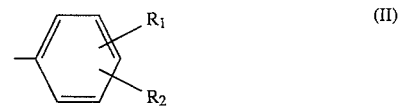

where $R_1$ and $R_2$ are each independently of the other hydrogen, halogen, $C_1$–$C_5$alkyl or phenyl, wherein at least 84% by weight of the particles have a Stokes equivalent diameter of <0.25 gm, and mixtures thereof.

Preferred are 1,4-diketopyrrolo[3,4-c]pyrroles of the formula I wherein at least 84% by weight of the pigment particles have a Stokes equivalent diameter of <0.20 μm, especially those wherein A and B are independently of each other radicals of the formulae

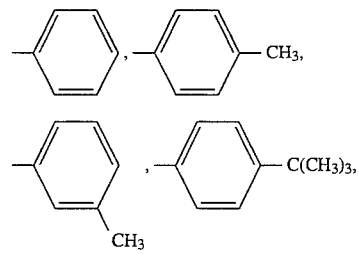

preferably

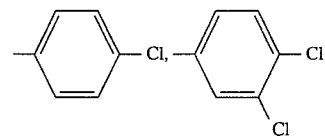

and particularly preferably

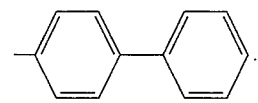

The $D_{max}$ value (Diameter of the maximum particle distribution) is <0.15 m. Electron micrographs (transmission) show that the bulk of the particles even have a size of ca 0.01–0.10 μm.

Preferably the radicals A and B are identical.

However, the invention can also comprise mixtures, which may be present as solid solutions or mixed crystals, of the just-described 1,4-diketopyrrolo[3,4-c]pyrroles, especially the solid solution mixture of the three 1,4-diketopyrrolo[3,4-c]pyrroles of the formulae

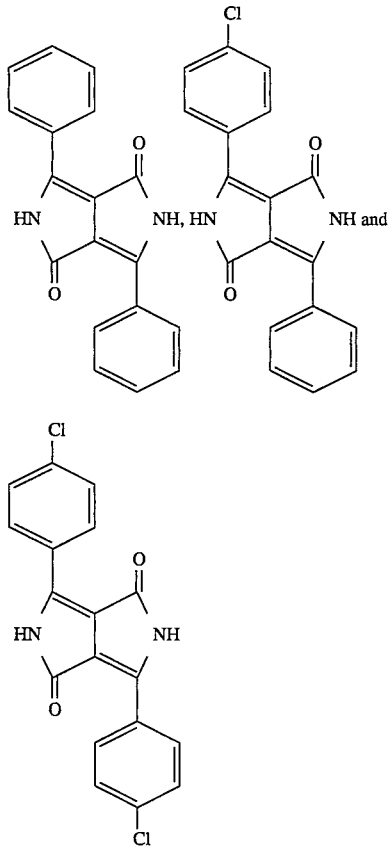

The characterizing X-ray diffraction diagram (determined by customary methods using a Siemens D 500®Röntgen-Diffractometer (CuK$_\alpha$ radiation) of the just-described solid solution is defined by the following

| Lattice spacings (d values in Å) | Relative intensity | Doubled glancing angle (2Θ) |
|---|---|---|
| 16.1 | 97.1 | 5.5 |
| 7.7 | 22.8 | 11.5 |
| 6.5 | 37.5 | 13.7 |
| 6.0 | 89.8 | 14.7 |
| 5.0 | 20.8 | 17.8 |

| Lattice spacings (d values in Å) | Relative intensity | Doubled glancing angle (2Θ) |
|---|---|---|
| 3.8 | 40.9 | 23.2 |
| 3.7 | 32.4 | 23.7 |
| 3.3 | 100.0 | 26.9 |
| 3.1 | 26.8 | 28.4 |
| 3.0 | 22.4 | 30.0. |

-continued

Very particular preference is given to the novel 1,4-diketopyrrolo[3,4-c]pyrroles A, B, C of the formulae

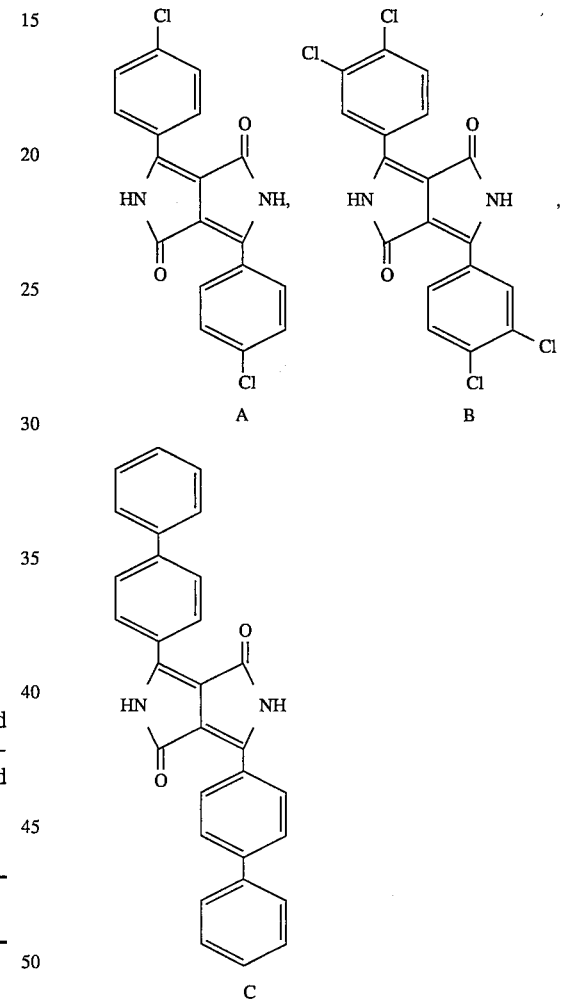

and to the solid solution D of the three pigments of the formulae

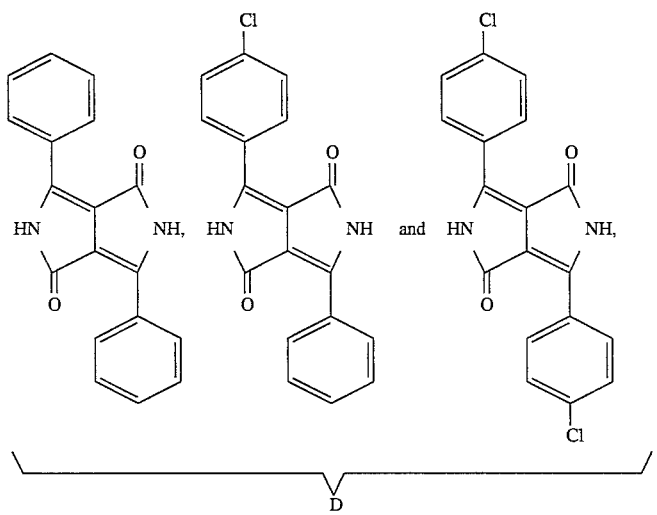

in particular those with a very high saturation characterized by the minimum chroma values reported in the table below. These are CIELAB chroma $C^*_{ab}$ values measured with a pigment concentration of 1% in a 1.0 mm thick compression-moulded masstone PVC-P sheet produced according to DIN 53775 Part 2 or Part 7 (6.2) (see Example 2 and Examples 4, 5 and 8):

| Pigment | $C_{ab}*$ |
|---|---|
| A | ≧42 |
| B | ≧42 |
| C | ≧14 |
| Solid solution D | ≧36 |

The present invention further provides the process for preparing the just-described 1,4-diketopyrrolo[3,4-c]pyrroles of the formula I by reacting 1 mol of a dicyclohexyl, dialkyl, alkyl phenyl or diphenyl succinate in which alkyl is $C_1$–$C_{18}$alkyl and phenyl is unsubstituted phenyl or phenyl substituted by one or two halogen atoms or one or two $C_1$–$C_6$alkyl or $C_1$–$C_6$alkoxy groups with 2 mol of a mixture of nitriles of the formulae

A-CN  (III)

and

B-CN  (IV), where A and B are each as defined above and ACN and BCN in the nitrile mixture are in a molar ratio of 100:0 to 50:50 relative to each other, in an inert organic solvent in the presence of an alkali metal or an alkali metal alkoxide as strong base at elevated temperature to form a pigment alkali metal salt and then liberating a compound of the formula I by protonating the resulting pigment alkali metal salt and subsequent conditioning, which comprises discharging the pigment alkali metal salt suspension into water and/or an alcohol ROH, where R is $C_1$–$C_4$alkyl, at a temperature between –20° and 50° C. in the presence of an acid and treating it likewise at a temperature between –20° C. and 50° C., preferably –10° to 40° C., for 10 minutes to 48 hours.

$C_1$–$C_6$Alkyl is for example methyl, ethyl, n-propyl, isopropyl, n-butyl, tert-butyl, amyl, hexyl and $C_1$–$C_{18}$alkyl is additionally for example heptyl, 2,2-dimethylhexyl, octyl, decyl, dodecyl, tetradecyl or octadecyl. $C_1$–$C_6$alkoxy is for example methoxy, ethoxy, n-propoxy, isopropoxy, butoxy or hexyloxy.

The acid can be added either before, together with or after the pigment salt suspension, preferably before or together with the pigment salt suspension.

It can be of advantage to use a buffer during the protonation, for example a phosphate, acetate, citric acid or triethanolamine buffer.

$C_1$–$C_4$Alkyl R is for example methyl, ethyl, propyl, isopropyl, n-butyl, tert-butyl. R is preferably methyl or ethyl.

$C_1$–$C_4$Alkyl radicals $R_1$ and $R_2$ are each for example methyl, ethyl, propyl, isopropyl, n-butyl, tert-butyl, n-pentyl or tert-amyl.

Halogens $R_1$ and $R_2$ are each in particular bromine and preferably chlorine.

Preferably the pigment alkali metal salt suspension is discharged into a water-alcohol mixture, and this mixture advantageously has a water:alcohol ratio of 80–20:20–80, preferably 70–30:30–70, in particular 65–35:35–65, % by volume.

The acids used as protonating agents comprise for example inorganic acids, for example hydrochloric acid, phosphoric acid and especially sulfuric acid, or aliphatic or aromatic carboxylic or sulfonic acids, e.g. formic acid, acetic acid, propionic acid, butyric acid, hexanoic acid, oxalic acid, benzoic acid, phenylacetic acid, benzensulfonic acid or p-toluenesulfonic acid, or mixtures thereof. Preferred organic acids are acetic acid and formic acid.

Protonation and conditioning are preferably carried out at temperatures between –10° and 30° C. over 1 to 8 hours.

The radicals A and B are subject to the previously indicated definitions and preferences.

The dialkyl or diphenyl succinates to be used can be symmetrical or asymmetrical diesters. Preferably, however, they are symmetrical diesters, especially symmetrical dialkyl esters.

In a diphenyl or phenyl alkyl succinate, phenyl can be for example unsubstituted phenyl or phenyl substituted by one or two halogen atoms, such as chlorine, $C_1$–$C_6$alkyl groups, such as methyl, ethyl, isopropyl or tert-butyl, or $C_1$–$C_6$alkoxy groups, such as methoxy or ethoxy. Phenyl is preferably unsubstituted phenyl. In a dialkyl or alkyl phenyl succinate, alkyl can be branched or unbranched, preferably branched, and preferably contains 1 to 12, in particular 1 to 8, particularly preferably 1 to 5, carbon atoms. Branched alkyl is preferably sec- or ten-alkyl, e.g. isopropyl, sec-butyl, ten-butyl or tert-amyl. Very particular preference is given to using symmetrical branched dialkyl succinates wherein each alkyl has 3 to 5 carbon atoms.

Examples of succinic diesters are dimethyl, diethyl, dipropyl, dibutyl, dipentyl, dihexyl, diheptyl, dioctyl, diisopropyl, di-sec-butyl, di-tert-butyl, di-tert-amyl, eli(1,1-dimethylbutyl), di(1,1,3,3-tetramethylbutyl), di(1,1-dimethylpentyl), eli(1-methyl-1-ethylbutyl), di(1,1-diethylpropyl), diphenyl, di(4-methylphenyl), di(2-methylphenyl), di(4-chlorophenyl), di(2,4-dichlorophenyl) and ethyl phenyl succinates.

The abovementioned succinic diesters and the nitriles of the formulae III and IV are known compounds and can be prepared by known methods.

The reaction of the succinic diester with the nitrile of the formula III or IV, or a mixture thereof, is carried out in an organic solvent. Suitable solvents include for example primary, secondary or tertiary alcohols having 1 to 10 carbon atoms, such as methanol, ethanol, n-propanol, isopropanol, n-butanol, sec-butanol, tert-butanol, n-pentanol, 2-methyl-2-butanol, 2-methyl-2-pentanol, 3-methyl-3-pentanol, 2-methyl-2-hexanol, 3-ethyl-3-pentanol and 2,4,4-trimethyl-2-pentanol, glycols, such as ethylene glycol or diethylene glycol, also ethers, such as tetrahydrofuran or dioxane, or glycol ethers, such as ethylene glycol monomethyl or dimethyl ether, ethylene glycol monoethyl or diethyl ether, diethylene glycol monomethyl ether or diethylene glycol monoethyl ether, also elipolar aprotic solvents, such as acetonitrile, benzonitrile, dimethylformamide, N,N-dimethylacetamide, nitrobenzene and N-methylpyrrolidone, aliphatic or aromatic hydrocarbons, such as benzene or alkyl-, alkoxy- or halogen-substituted benzene, such as toluene, xylenes, anisole or chlorobenzene, or aromatic N-heterocycles, such as pyridine, picoline or quinoline. It is in addition also possible to use the nitrile reactant of the formula HI or IV in excess as solvent, provided it is liquid within the temperature range within which the reaction takes place. The abovementioned solvents can also be used in the form of mixtures. Preference is given to using 5–20 parts by weight of solvent per 1 part by weight of the reactants.

In the process of the invention the solvent used is preferably an alcohol, in particular a secondary or tertiary alcohol. Preferred tertiary alcohols are tert-butanol and tert-amyl alcohol. Also of considerable interest are mixtures thereof or mixtures of these preferred solvents with aromatic hydrocarbons, such as toluene or xylenes, or with halogen-substituted benzenes, such as chlorobenzene or o-dichlorobenzene.

Suitable strong bases include alkali metals, such as lithium, sodium and potassium, and alkali metal alkoxides derived in particular from primary, secondary or tertiary aliphatic alcohols having 1 to 10 carbon atoms, e.g. lithium, sodium or potassium methoxide, ethoxide, n-propoxide, isopropoxide, n-butoxide, sec-butoxide, tert-butoxide, 2-methyl-2-butoxide, 2-methyl-2-pentoxide, 3-methyl-3-pentoxide and 3-ethyl-3-pentoxide. However, it is also possible to use a mixture of the abovementioned alkali metal alkoxides. Preference is given to using alkali metal alkoxides, the alkali metal being especially sodium or potassium, and the alkoxide is preferably derived from a secondary or tertiary alcohol. Particularly preferred strong bases are therefore for example sodium or potassium isopropoxide, sec-butoxide, tert-butoxide and tert-pentoxide. These alkali metal alkoxides can also be prepared in situ by reacting the corresponding alcohol with the alkali metal.

In the process of the invention, the strong base can be used for example in an amount from 0.1 to 10 mol, preferably from 1.9 to 4.0 mol, based on 1 mol of the succinic diester. Although in principle stoichiometric amounts of base are sufficient, excess base does in many cases have a favourable effect on the yield.

The reaction can be carded out for example at a temperature from 60° to 140° C, preferably from 80° to 120° C.

To react the succinic diester with the nitrile(s) of the formulae III and IV it is possible in principle to introduce all the components together at a lower temperature and then to heat the mixture up to within the range of the reaction temperature, or to add the individual components in the region of the reaction temperature in any desired order. A preferred embodiment, which generally has a particularly favourable effect on the yield, consists in initially charging the nitrile together with the strong base and to meter in the succinic diester in the region of the reaction temperature. A further possibility is to meter the succinic diester and the nitrile simultaneously into the initially charged base. It is entirely possible to carry out the process of the invention not only batchwise but also continuously.

Especially in the case of succinic diesters with lower alkyl radicals and in the case of alkoxides derived from lower alcohols, e.g. methanol, ethanol, n-propanol, isopropanol or tert-butanol, it can be advantageous to remove the lower alcohol reaction product continuously from the reaction medium to obtain higher yields.

If the solvent used is an alcohol and the base an alkoxide, it can be advantageous for the alcohol and the alkoxide to have the same alkyl moiety. It can similarly be advantageous if, in addition, the succinic diester contains precisely such alkyl groups.

To protonate the pigment salts obtained, either the pigment alkali metal salt can be added to the protonating agent of the invention, which consists of water and/or alcohol and the acid, or the pigment alkali metal salt and the acid can be added simultaneously to the water and/or alcohol, or the acid can be added to the water and/or alcohol only after the pigment alkali metal salt suspension has been added. The water and/or alcohol can be used in any desired mixing ratio between 5 and 20 parts by weight per 1 part of the pigment alkali metal salt formed. The acid is advantageously used, depending on the temperature and the starting material, in an amount of from 0.5 to 3, preferably 1 to 2, equivalents, based on the base employed, preferably in a sufficient amount to obtain pH <10 at the end of the protonation.

In the preparation of the abovementioned 1,4-diketopyrrolo[3,4-c]pyrroles of the formulae

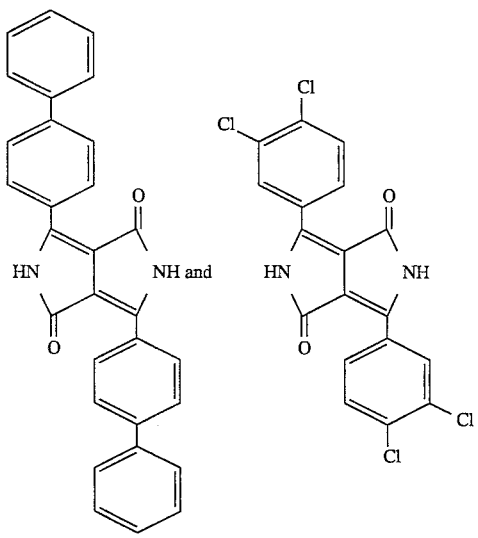

good results can be obtained even without the addition of acid.

After protonation, the compounds of the formula I precipitate and can be isolated by separating methods known per se, such as filtration.

The compounds of the formula I can be used as pigments for macromolecular organic materials. In fact, the pigments can mostly be used directly in the pigmentary form as produced by the process of the invention. Their crystal morphology may if necessary be further optimized according to the intended use by one of the numerous customary subsequent treatments.

Depending on the intended use, it can be of advantage to prepare mixtures of the compounds of the formula I. This can be achieved for example by mixing mutually independently prepared, different reaction solutions prior to protonation, protonating them together and then isolating the product obtained, or else by using not one but two different nitriles in the preparation. In many cases solid solution or mixed crystals are formed thereby.

Macromolecular organic materials which can be coloured/pigmented with the compounds of the formula I include for example cellulose ethers and esters, such as ethylcellulose, nitrocellulose, cellulose acetate and cellulose butyrate, natural resins and synthetic resins such as chain growth or step growth polymer resins, for example amino resins, especially urea- and melamine-formaldehyde resins, alkyd resins, phenolic resins, polycarbonates, polyolefins, such as polyethylene and polypropylene, polystyrene, polyvinyl chloride, polyacrylonitrile, polyacrylic esters, polyamides, polyurethanes, polyesters, rubber, casein, silicone and silicone resins, individually or mixed.

It is immaterial in this connection whether the macromolecular organic compounds mentioned are present as plastics, melts or in the form of spinning solutions, varnishes, paints or printing inks. Depending on the intended use, it is advantageous to use the compounds of the formula I as toners or in the form of preparations. Based on the macromolecular organic material to be pigmented, the compounds of the formula I can be used in an amount of from 0.01 to 30% by weight, preferably 0.1 to 20% by weight.

Depending on the conditioning process or application, it can be of advantage to add to the pigment certain amounts of texture-improving agents before or after the conditioning process, provided they have no adverse effect in the use of the pigments according to the invention (especially in polyethylene). Suitable texture improvers include in particular fatty acids having at least 18 carbon atoms, such as stearic or behenic acid or their amides or metal salts, in particular magnesium salts, such as plasticizers, waxes, resin acids, such as abietic acid, rosin soap, alkylphenols or aliphatic alcohols, such as stearic alcohol or aliphatic 1,2-dihydroxy compounds having 8 to 22 carbon atoms, such as 1,2-dodecanediol, also modified rosin maleate resins or fumaric acid rosin resins. The texture improvers are preferably added in amounts of 0.1–30% by weight, in particular 2–15% by weight, based on the end product. The abovementioned 1,2-dihydroxy compounds, especially 1,2-dodecanediol, can also be used for improving the filtration of the suspended pigment composition.

The colourings obtained, for example in plastics, fibres, varnishes or prints, combine a remarkably high hue purity and transparency with high colour strength, good dispersibility, good overspraying, migration, heat, light and weathering fastness, and also with high gloss.

The compounds of the formula I of the invention, however, are as mentioned above very particularly noteworthy for excellent purity of hue and for their high transparency. Accordingly they are preferably suitable for colouring plastics, printing inks and aqueous and/or solvent-containing coatings, in particular automotive coatings. Very particular preference is given to their use for metallic effect coatings (metal or mica).

The examples which follow illustrate the invention. Percentages are by weight, unless otherwise stated.

EXAMPLE 1

A sulfonation flask is charged with 450 ml of tert-amyl alcohol under nitrogen. 29.9 g of sodium are added and the mixture is heated to 95°–102° C. The molten sodium is then maintained overnight at 100°–105° C. with vigorous stirring. To the resulting solution are then added 33.8 g of benzonitrile and 44.8 g of 4-chlorobenzonitrile. Subsequently 86.0 g of diisopropyl succinate are metered in at 105°–110° C. over 5 hours, the resulting isopropanol is distilled off at the same time and t-amyl alcohol is added continuously as a replacement. The reaction mixture is further stirred for 2 hours, cooled down to room temperature and additionally diluted with 100 ml of tert-amyl alcohol. Then the reaction mixture is discharged onto a mixture of 345 ml of water, 345 ml of methanol and 70 ml of concentrated sulfuric acid at 20° C. and the resulting mixture is subsequently stirred at 25° C. for 4 hours.

The dark red mixture is filtered, and the pigment is washed with methanol and water and dried at 80° C. in a vacuum drying cabinet to leave 87.8 g of a red powder.

| Analysis: | C | H | N | Cl |
|---|---|---|---|---|
| Calculated*: | 67.0% | 3.4% | 8.7% | 11.0% |
| Found: | 66.7% | 3.4% | 8.6% | 11.2% |

*assuming equal reactivity between the two nitriles

Particle size distribution:

84% by weight of the pigment particles have a Stokes equivalent diameter D 84 of <0.14 μm. The $D_{max}$ value is 0.10 μm.

EXAMPLE 2

Example 1 is repeated using 25.4 g of sodium, 315 ml of t-amyl alcohol, 28.8 g of benzonitrile, 38.1 g of 4-chlorobenzonitrile, 72.6 g of succinic acid and 56.4 g of concentrated sulfuric acid. This yields 76.1 g of a red powder.

| Analysis:   | C     | H    | N    | Cl    |
|-------------|-------|------|------|-------|
| Calculated*:| 67.0% | 3.4% | 8.7% | 11.0% |
| Found:      | 66.6% | 3.4% | 8.6% | 11.1% |

*assuming equal reactivity between the two nitrites

Particle size distribution:

84% by weight of the pigment particles have a Stokes equivalent diameter D 84 of <0.11 µm. The $D_{max}$ value is 0.09 µm.

Saturation (chroma):

The product obtained is used to prepare, by the method laid down in DIN 53775 Part 2 and Part 7 (6.2), a compression-moulded PVC-P sheet 1.0 mm in thickness (cf. Item 6.3 of DIN 53775 Part 2) with a pigment concentration of 1%, and the chroma ($C^*_{ab}$) value according to CIELAB is determined. All colour measurements were carded out using a Minolta CM-2002® spectrophotometer (d/8 geometry, measurement above white with inclusion of gloss, illuminant D 65, observer 10°). 1% of pigment in a compression-moulded masstone PVC-P sheet 1.0 µm in thickness has a chroma $C^*_{ab}$ of 4.16.

EXAMPLE 3

A sulfonation flask is charged with 170 ml of tert-amyl alcohol under nitrogen. 11.04 g of sodium are added and the mixture is heated to 92°–102° C. The molten sodium is maintained overnight at 100°–107° C. with vigorous stirring. Into the resulting solution are then metered 44.02 g of 4-chlorobenzonitrile and 37.2 g of diisopropyl succinate, dissolved in 50 ml of tert-amyl alcohol at 80° C., over 2 hours at 80°–98° C. The reaction mixture is further stirred at 80° C. for 3 hours and at the same time 4.88 g of diisopropyl succinate are added dropwise. Then the reaction mixture is cooled down to room temperature, added to a mixture of 270 ml of methanol, 200 ml of water and 48.1 g of concentrated sulfuric acid at 20° C., and stirring is continued at 20° C. for 6 hours. The red mixture is filtered, and the residue is washed with methanol and water and dried at 80° C. in a drying cabinet to leave 46.7 g of a red powder.

| Analysis:   | C      | H     | N     | Cl     |
|-------------|--------|-------|-------|--------|
| Calculated: | 60.50% | 2.82% | 7.84% | 19.85% |
| Found:      | 60.36% | 2.85% | 7.69% | 19.61% |

Particle size distribution:

84% by weight of the pigment particles have a Stokes equivalent diameter D 84 of <0.14 µm. The $D_{max}$ value is 0.11 µm.

EXAMPLE 4

A sulfonation flask is charged with 170 ml of tert-amyl alcohol under nitrogen. 11.04 g of sodium are added and the mixture is heated to 92°–102° C. The molten sodium is maintained overnight at 100°–107° C. with vigorous stirring. To the resulting solution are then added dropwise 44.2 g of 4-chlorobenzonitrile and 37.2 g of diisopropyl succinate, dissolved in 50 ml of tert-amyl alcohol at 80° C., over 2 hours at 80°–98° C. The reaction mixture is further stirred at 80° C. for 3 hours and at the same time 4.88 g of diisopropyl succinate are added dropwise. Then the reaction mixture is cooled down to room temperature, added to a mixture of 170 ml of methanol, 320 ml of water and 48.1 g of concentrated sulfuric acid at 0° C., and stirring is continued at 0° C. for 6 hours. The red mixture is filtered, and the residue is washed with methanol and water and dried at 80° C. in a vacuum drying cabinet to leave 45.5 g of a red powder.

| Analysis:   | C      | H     | N     | Cl     |
|-------------|--------|-------|-------|--------|
| Calculated: | 60.50% | 2.82% | 7.84% | 19.85% |
| Found:      | 60.32% | 2.90% | 7.84% | 19.55% |

Particle size distribution:

84% by weight of the pigment particles have a Stokes equivalent diameter D 84 of <0.17 µm. The $D_{max}$ value is 0.10 µm.

Saturation (chroma):

1% of pigment in a compression-moulded masstone PVC-P sheet 1.0 mm in thickness has a chroma $C^*_{ab}$ of 45.7.

EXAMPLE 5

A sulfonation flask is charged with 190 ml of tert-amyl alcohol under nitrogen. 10.6 g of sodium are added and the mixture is heated to 92°–102° C. The molten sodium is maintained overnight at 100°–107° C. with vigorous stirring. To the resulting solution are then added 41.22 g of 4-biphenylnitrile at 85°–90° C. The reaction mixture is reheated to 105°–110° C. and 27.9 g of diisopropyl succinate are added dropwise over 6 hours. The reaction mixture is further stirred at 100° C. for 3 hours. Then the reaction mixture is cooled down to room temperature, added to a mixture of 160 ml of methanol, 140 ml of water and 46.0 g of concentrated sulfuric acid at 0° C., and stirring is continued at the same temperature for 5 hours. The violet mixture is filtered, and the residue is washed with methanol and water and dried at 80° C. in a vacuum drying cabinet to leave 43.4 g of a dark red powder.

| Analysis:   | C      | H     | N     |
|-------------|--------|-------|-------|
| Calculated: | 81.80% | 4.58% | 6.36% |
| Found:      | 81.17% | 4.60% | 6.25% |

Particle size distribution:

84% by weight of the pigment particles have a Stokes equivalent diameter D 84 of <0.21 µm. The Dmax value is 0.11 µm.

Saturation (chroma):

1% of pigment in a compression-moulded masstone PVC-P sheet 1.0 mm in thickness has a chroma $C^*_{ab}$ of 15.8.

EXAMPLE 6

A sulfonation flask is charged with 200 ml of tert-amyl alcohol under nitrogen. 16.14 g of sodium are added and the mixture is heated to 92°–102° C. The molten sodium is maintained overnight at 100°–107° C. with vigorous stirring. To the resulting solution are then added 41.94 g of 3-tolunitrile at 95°–100° C. The reaction mixture is reheated to 105°–110° C. and 46.14 g of diisopropyl succinate are added dropwise over 5 hours. The reaction mixture is further stirred at 100° C. for 3 hours. Then the reaction mixture is cooled down to room temperature, added to a mixture of 190 ml of methanol, 190 ml of water and 71.6 g of concentrated sulfuric acid at 0° C., and stirring is continued at 0° C. for 5 hours. The red mixture is filtered, and the residue is washed with methanol and water and dried at 80° C. in a vacuum drying cabinet to leave 40.9 g of a red powder.

| Analysis:   | C      | H     | N     |
|-------------|--------|-------|-------|
| Calculated: | 75.93% | 5.10% | 8.85% |
| Found:      | 75.82% | 2.23% | 8.71% |

Particle size distribution:

84% by weight of the pigment particles have a Stokes equivalent diameter D 84 of <0.16 μm. The $D_{max}$ value is 0.13 μm.

EXAMPLE 7

A sulfonation flask is charged with 200 ml of tert-amyl alcohol under nitrogen. 9.2 g of sodium are added and the mixture is heated to 92°–102° C. The molten sodium is maintained overnight at 100°–107° C. with vigorous stirring. To the resulting solution are then added 31.24 g of 4-tolunitrile at 85°–90° C. The reaction mixture is reheated to 95° C. and 32.36 g of diisopropyl succinate are added dropwise over 6 hours. The reaction mixture is further stirred at 95° C. for 2 hours. Then the reaction mixture is cooled down to room temperature, added to a mixture of 180 ml of methanol, 180 ml of water and 40.8 g of concentrated sulfuric acid at 0° C., and stirring is continued at 0° C. for 5 hours. The red mixture is filtered, and the residue is washed with methanol and water and dried at 80° C. in a vacuum drying cabinet to leave 19.8 g of a red powder.

| Analysis:   | C      | H     | N     |
|-------------|--------|-------|-------|
| Calculated: | 75.93% | 5.10% | 8.86% |
| Found:      | 75.57% | 5.11% | 8.63% |

Particle size distribution:

84% by weight of the pigment particles have a Stokes equivalent diameter D 84 of <0.18 μm. The $D_{max}$ value is 0.14 μm.

EXAMPLE 8

A sulfonation flask is charged with 200 ml of tert-amyl alcohol under nitrogen. 10.3 g of sodium are added and the mixture is heated to 92°–102° C. The molten sodium is maintained overnight at 100°–107° C. with vigorous stirring. To the resulting solution are then added 38.5 g of 3,4-dichlorobenzonitrile after cooling down to 80° C. 29.4 g of diisopropyl succinate are then added dropwise at 80° C. over 2½ hours. After further stirring at 80° C. for 2 hours the reaction mixture is cooled down to room temperature, added to a mixture of 160 ml of methanol, 160 ml of water and 11.4 g of concentrated sulfuric acid at 50° C., and stirring is continued at 50° C. for 4 hours. The red mixture is filtered, and the residue is washed with methanol and water and dried at 80° C. in a vacuum drying cabinet to leave 40.6 g of a red powder.

| Analysis:   | C      | H     | N     | Cl     |
|-------------|--------|-------|-------|--------|
| Calculated: | 50.74% | 1.89% | 6.57% | 33.28% |
| Found:      | 49.12% | 2.18% | 6.21% | 29.15% |

Particle size distribution:

84% by weight of the pigment particles have a Stokes equivalent diameter D 84 of <0.06 μm. The $D_{max}$ value is 0.04 μm.

Saturation (chroma):

1% of pigment in a compression-moulded masstone PVC-P sheet 1.0 mm in thickness has a chroma $C^*_{ab}$ of 45.2.

EXAMPLE 9

A sulfonation flask is charged with 450 ml of tert-amyl alcohol under nitrogen. 26.5 g of sodium are added and the mixture is heated to 92°–102° C. The molten sodium is maintained overnight at 100°–107° C. with vigorous stirring. To the resulting solution are then added 111.0 g of 4-biphenylnitrile. 69.8 g of diisopropyl succinate are added dropwise over 4 hours at 105°–110° C. The reaction mixture is further stirred at 82° C. for 9 hours. Then the reaction mixture is cooled down to room temperature, added dropwise to a mixture of 1100 ml of methanol, 250 ml of water and 47.0 g of 60% sulfuric acid at 26°–45° C., and stirring is continued at 45° C. for 5 hours. The mixture is filtered and the residue is washed with methanol and water and dried at 80° C. in a vacuum drying cabinet to leave 100.6 g of a dark red powder.

| Analysis:   | C      | H     | N     |
|-------------|--------|-------|-------|
| Calculated: | 81.80% | 4.58% | 6.36% |
| Found:      | 80.10% | 4.57% | 6.26% |

Particle size distribution:

84% by weight of the pigment particles have a Stokes equivalent diameter D 84 of <0.13 μm. The $D_{max}$ value is 0.11 μm.

EXAMPLE 10

5 g of the pigment of Example 1, 56.56 g of the alkyd resin ®ALKYDAL F310 (Bayer), 60% in xylene, 21.70 g of xylene, 0.94 g of silicone oil (1% in xylene) and 13.55 g of the melamine resin ®CYMEL 327 (Cyanamid), 90% in isobutanol, are dispersed together in a shaker (®Skandex disperser BA-S 20 in line with DIN 53238 Part 10) until stage 6 (DIN 53238 Part 24) is reached, however not longer than 4 hours.

The masstone coating thus obtained can after dilution by customary methods be used for determining the particle size distribution by photosedimentometry (cf. Herbst & Hunger, Industrielle Organische Pigmente, VCH 1987, pp. 32–34 and 40–43 and K. Brugger, Powder Technology 13, 215–221 (1976). The particle size distributions are measured using a Joyce-Loebl Disc Centrifuge Photodensitometer 4 (DCF 4) according to standard procedures (see e.g. K. Brugger, Powder Technology 13, 215–221 (1976)); K. Brugger, Powder Technology 14, 187–188 (1976); F. K. Hansen in: ACS Symp. Ser. 471 (Particle Size Distribution II), pp. 169–183 (1991); R. Finsy et al., in; Acvances in Measurement and Control of Colloidal Processes, Int. Symp., Butterworth, London (1991); Instruction manual of the DCF 4, Joyce-Loebl Ltd., Gateshead, UK). 0.5 ml of diluted (dilution 1:39 with an organic medium adapted to the test paint) and ultrasonified (tip sonifier Branson B 12, 60 sec, output power 100 W) test paint is layered on top of 15 ml of spinfluid. The spinfluid consists of a density gradient of 20% to 40% (w/w) tetrachloroethylene in the adapted medium at room temperature and is formed using a gradient former (W. Alex, Thesis, University of Karlsruhe (1972). The DCF 4 is run at 10000 rpm. The extinktion of white light is due to scattering and/or absorption by particles passing through the light beam near the bottom of the disc cavity. The transmitted light, detected by a photodiode, is recorded as a function of time ca. every 0.1 sec (total run time ca. 40 minutes). Time values are convened to particle sizes using Stokes law of sedimentation, whereas transmission data are convened to relative masses using Mie theory (wavelength averaged extinction efficiency factors; see F. K. Hansen in: ACS Symp. Ser. 471 (Particle Size Distribution II), pp. 169–183 (1991); Light Scattering by Small Particles, H. C. van de Hulst, Wiley, London (1957); H. Reicheft, Powder Technology 6, 366–366 (1972). Before conversion, each pair of data values is calculated as an average of 1 to approx. 1000 of single measurements in order to optimize the signal-to-noise ratio. On evaluation, the dependency of the spinfluid viscosity and density on the temperature is taken into consideration. In the present case at least 84% by weight of the particles have a Stokes equivalent diameter D 84 of <0.25 µm.

The masstone coating obtained can also be applied to a transparent polyethylene film with a wire-wound drawbar (100 µm wet film thickness). The coating is then flashed off at room temperature for 15 minutes and subsequently baked at 115° C. for 30 minutes.

EXAMPLE 11

7.5g of the pigment of Example 1, 98.9 g of CAB solution consisting of

| | |
|---|---|
| 41.0 g | of cellulose acetobutyrate ® CAB 531.1, 20% in butanol/xylene 2:1 (Eastman Chem.) |
| 1.5 g | of zirconium octoate, |
| 18.5 g | of ® SOLVESSO 150* (ESSO). |
| 21.5 g | of butyl acetate, and |
| 17.5 g | of xylene, |

*Aromatic hydrocarbons 36.5 g of the polyester resin ®DYNAPOL H700 (Dynamit Nobel), 4.6 g of the melamine resin MAPRENAL MF650 (Hoechst) and 2.5 g of the dispersant ®DISPERBYK 160 (Byk Chemic) are dispersed together using a shaker for 90 minutes (total coating 150 g; 5% of pigment).

27.69 g of the masstone coating thus obtained are mixed for base-coat application with 17.31 g of aluminium stock solution (8% ) consisting of

| | |
|---|---|
| 12.65 g | of ® SILBERLINE SS 3334AR, 60% (Silberline Ltd.) |
| 56.33 g | of CAB solution (composition as above) |
| 20.81 g | of polyester resin ® DYNAPOL H700 |
| 2.60 g | of melamine resin ® MAPRENAL MF650 |
| 7.59 g | of ® SOLVESSO 150 | and sprayed onto an aluminium panel (wet film thickness about 20 µm). After a flash-off time of 30 minutes at room temperature a TSA varnish consisting of

| | |
|---|---|
| 29.60 g | of acrylic resin ® URACRON 2263 XB, 50% in xylene/butanol (Chem. Fabrik Schweizerhalle), |
| 5.80 g | of melamine resin ® CYMEL 327, 90% in isobutanol, |
| 2.75 g | of butylglycol acetate, |
| 5.70 g | of xylene, |
| 1.65 g | of n-butanol, |
| 0.50 g | of silicone oil, 1% in xylene, |
| 3.00 g | of photostabilizer ® TINUVIN 900, 10% in xylene (Ciba) |
| 1.00 g | of photostabilizer ® TINUVIN 292, 10% in xylene (Ciba) | is sprayed on as top coat (wet film thickness about 50 µm). Subsequently the coating is flashed off at room temperature for 30 minutes and then baked at 130° C. for 30 minutes.

What is claimed is:

1. Finely divided 1,4-diketopyrrolo[3,4-c]pyrroles of the formula

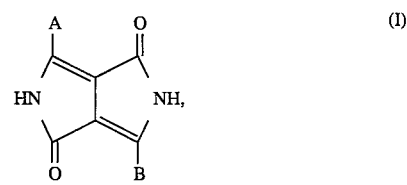

where A and B are each independently of the other a radical of the formula

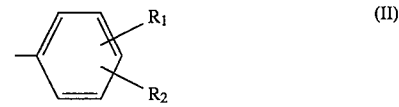

where $R_1$ and $R_2$ are each independently of the other hydrogen, halogen, $C_1$–$C_5$ alkyl or phenyl, wherein at least 84% by weight of the particles have a Stokes equivalent diameter of $\leq 0.25$ µm, and mixtures thereof.

2. 1,4-Diketopyrrolo[3,4-c]pyrroles of the formula I according to claim 1, wherein at least 84% by weight of the particles have a Stokes equivalent diameter of $\leq 0.20$ µm.

3. 1,4-Diketopyrrolo[3,4-c]pyrroles according to claim 2, wherein, in the formula I, A and B are independently of each other radicals of the formulae

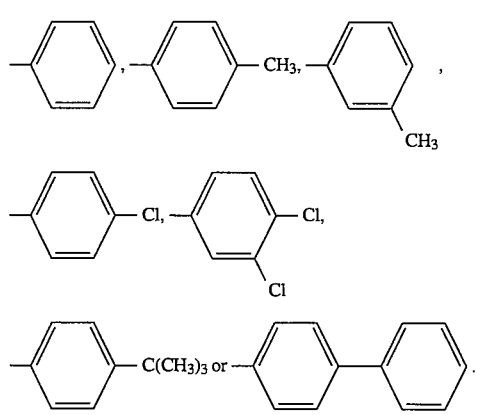

4. 1,4-Diketopyrrolo[3,4-c]pyrroles according to claim 2, wherein, in the formula I, A and B are identical and are radicals of the formulae

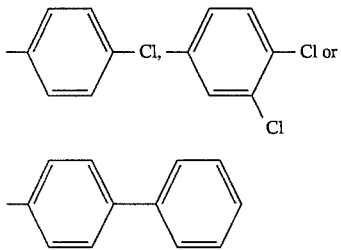

5. 1,4-Diketopyrrolo[3,4-c]pyrroles according to claim 2, comprising a solid solution of the compounds of the formulae

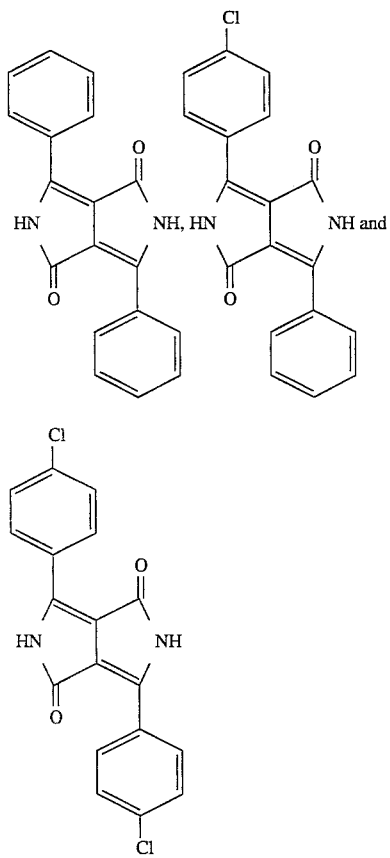

6. A 1,4-diketopyrrolo[3,4-c]pyrrole of the formula

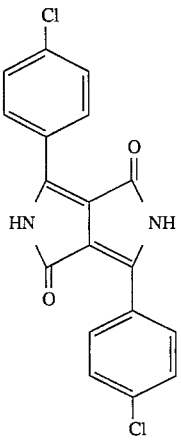

according to claim 2, having a CIELAB chroma $C^*_{ab} \geq 42$ in 1% concentration in a 1.0 mm thick compression-moulded masstone PVC-P sheet produced according to DIN 53775 Parts 2 and 7.

7. A 1,4-diketopyrrolo[3,4-c]pyrrole of the formula

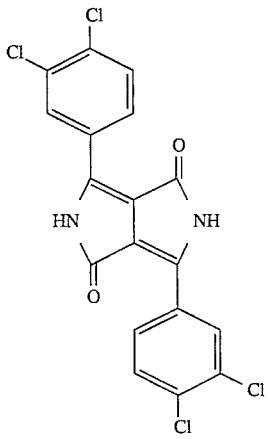

according to claim 2, having a CIELAB chroma $C^*_{ab} \geq 42$ in 1% concentration in a 1.0 mm thick compression-moulded masstone PVC-P sheet produced according to DIN 53775 Parts 2 and 7.

8. A 1,4-diketopyrrolo[3,4-c]pyrrole of the formula

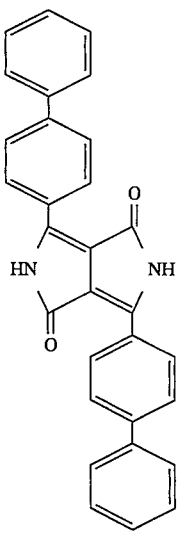

according to claim 2, having a CIELAB chroma $C^*_{ab} \geq 14$ in 1% concentration in a 1.0 mm thick compression-moulded masstone PVC-P sheet produced according to DIN 53775 Parts 2 and 7.

9. The solid solution of the 1,4-diketopyrrolo[3,4-c]pyrroles according to claim 5, having a CIELAB chroma $C^*_{ab} > 36$ in 1% concentration in a 1.0 mm thick compression-moulded masstone PVC-P sheet produced according to DIN 53775 Parts 2 and 7.

10. A process for preparing 1,4-diketopyrrolo[3,4-c]pyrroles of the formula I according to claim 1 by reacting in a 1:2 molar ratio 1 mol of dicyclohexyl, dialkyl, alkyl phenyl or diphenyl succinate in which alkyl is $C_1$–$C_{18}$alkyl and phenyl is unsubstituted phenyl or phenyl substituted by one or two halogen atoms or one or two $C_1$–$C_6$alkyl or $C_1$–$C_6$alkoxy groups with 2 mol of a mixture of nitriles of the formulae

A-CN     (III)

and

B-CN,     (IV)

where A and B are each as defined above and ACN and BCN in the nitrile mixture are in a molar ratio of 100:0 to 50:50 relative to each other, in an inert organic solvent in the presence of an alkali metal or an alkali metal alkoxide as strong base at a temperature of from about 60° C. to about 140° C. to form a pigment alkali metal salt and then liberating a compound of formula I by protonating the resulting pigment alkali metal salt and subsequent conditioning, which comprises discharging the pigment alkali metal salt suspension into water and/or an alcohol ROH, where R is $C_1$–$C_4$alkyl, at a temperature between −20° C. and 50° C. in the presence of an acid and treating it likewise at a temperature between −20° C. and 50° C. for 10 minutes to 48 hours.

11. A process according to claim 10, wherein the acid is added to the water and/or alcohol before or together with the alkali metal pigment salt suspension.

12. A process according to claim 10, wherein the radicals A and B are each independently of the other

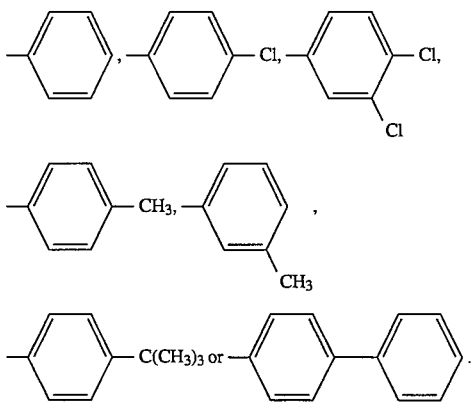

13. A process according to claim 10, wherein the radicals A and B are identical.

14. A process according to claim 10, wherein a mixture of water and alcohol in a ratio of 80–20:20–80% by volume is used.

15. A process according to claim 10, wherein the alcohol is methanol or ethanol.

16. A process according to claim 10, wherein the acid is used in a sufficient amount to obtain pH<10 at the end of the protonation.

17. A process according to claim 10, wherein the protonation is effected using an inorganic acid selected from hydrochloric acid, sulfuric acid and phosphoric acid.

18. A process according to claim 10, wherein the protonation is effected using an aliphatic or aromatic carboxylic or sulfonic acid selected from formic acid, acetic acid, propionic acid, butyric acid, hexanoic acid, oxalic acid, benzoic acid, phenylacetic acid, benzenesulfonic acid and p-toluenesulfonic acid.

19. A process according to claim 17, wherein sulfuric acid is used.

20. A process according to claim 18, wherein acetic acid or formic acid are used.

21. A process according to claim 10, wherein the protonating agent is used in any desired mixing ratios between 5 and 20 parts by weight of the protonating agent per 1 part of the alkali metal pigment salt.

22. A process according to claim 10, wherein protonation and conditioning are carried out at a temperature between −10° and 30° C.

* * * * *